(12) United States Patent
Park et al.

(10) Patent No.: US 8,460,162 B2
(45) Date of Patent: Jun. 11, 2013

(54) ROBOT FOR GAIT TRAINING AND OPERATING METHOD THEREOF

(75) Inventors: Kwang Hoon Park, Seoul (KR); Kyung Hwan Lee, Gyeonggi-do (KR)

(73) Assignee: P & S Mechanics Co., Ltd., Seoul (KR)

( * ) Notice: Subject to any disclaimer, the term of this patent is extended or adjusted under 35 U.S.C. 154(b) by 371 days.

(21) Appl. No.: 12/895,281

(22) Filed: Sep. 30, 2010

(65) Prior Publication Data

US 2011/0071442 A1   Mar. 24, 2011

Related U.S. Application Data

(63) Continuation-in-part of application No. PCT/KR2009/001533, filed on Mar. 26, 2009.

(30) Foreign Application Priority Data

Mar. 31, 2008   (KR) .......................... 10-2008-0029605

(51) Int. Cl.
  *A63B 71/60*   (2006.01)
(52) U.S. Cl.
  USPC .......................... 482/54; 482/1; 482/8; 482/51
(58) Field of Classification Search
  USPC ............................................ 482/1–9, 54, 57
  See application file for complete search history.

(56) References Cited

U.S. PATENT DOCUMENTS

| 6,666,831 B1 | 12/2003 | Edgerton et al. | |
| 6,689,075 B2 | 2/2004 | West | |
| 7,331,906 B2 | 2/2008 | He et al. | |
| 2002/0022554 A1* | 2/2002 | Borsheim | 482/54 |
| 2004/0005962 A1* | 1/2004 | Borsheim | 482/54 |

FOREIGN PATENT DOCUMENTS

KR   10-2007-0105605   10/2007

OTHER PUBLICATIONS

International Search Report in PCT/KR2009/001533, dated Oct. 29, 2009.
Written Opinion in PCT/KR2009/001533, dated Oct. 29, 2009.

* cited by examiner

*Primary Examiner* — Stephen Crow
(74) *Attorney, Agent, or Firm* — Womble Carlyle

(57) ABSTRACT

A robot for gait training includes a walking-assist robot (100) to be put on legs of a walking trainee; a treadmill (200; a load-hoist (300) for supporting the body of the walking trainee; and a controller (400). The controller (400) includes an input unit (410) for receiving or inputting information or commands, and a speed, angle and rotational force of each joint required for training of the walking trainee, an information storage device for selectively storing the information and commands received through the input unit (410), a control unit for controlling the walking-assist robot (100), the treadmill (200) and the load hoist (300) according to the information or commands input through the input unit (410) or transmitted from the information storage device, and a monitor (420) for displaying the information transmitted from the walking-assist robot (100), the treadmill (200), the load hoist (300) and the information storage device.

9 Claims, 16 Drawing Sheets

<Hip joint angle/speed tracking curve>

< Knee joint angle/speed tracking curve>

<Knee joint angle pattern of right leg>

<Knee joint angle pattern of right leg>

<Hip joint angle pattern tracking>

<Knee joint angle pattern tracking>

<Ankle joint angle pattern tracking>

<Hip/knee/ankle joints synchronization
angle pattern tracking>

<Pattern change of hip join>

<Pattern change of knee joint>

<Pattern change of ankle joint>

ROBOT FOR GAIT TRAINING AND OPERATING METHOD THEREOF

CROSS REFERENCE TO RELATED APPLICATIONS

This is a Continuation-in-Part of international application Ser. No. PCT/KR2009/001533, filed Mar. 26, 2009, which published as WO 2009/145423A1 and claims priority to Korean Patent Application No. KR 10-2008-0029605, filed on Mar. 31, 2008. The contents of the aforementioned applications are incorporated by reference in their entirety.

BACKGROUND OF THE INVENTION

1. Field of the Invention

The present invention relates to a robot for gait training and an operating method thereof, and more particularly, to a robot for gait training and an operating method thereof for the purpose of rehabilitation of patients with walking disability.

2. Description of the Related Art

Patients with walking disability perform gait training by bending their legs or moving according to walking patterns guided by walking-assist robots put on their bodies. During gait training using the walking-assist robot, if any one of an angle, speed and torque of each joint among hip joints, knee joints and ankle joints is out of a standardized walking pattern appropriate for training for walking trainees, this means that the walking trainee is not performing the gait training according to a walking pattern appropriate for the rehabilitation training.

In a conventional art, walking trainees perform the gait training by driving walking-assist robots at a designated angle and speed while wearing the walking-assist robots on their legs. However, since it is difficult to determine whether the trainee performs the gait training in an appropriate walking pattern on the basis of movement of the legs at the designated angle and speed and to determine what training pattern is more appropriate for the walking trainee, effective gait training has been hard to achieve.

In addition, since the walking trainees wearing the walking-assist robots and performing the gait training have different body sizes, the conventional walking-assist robot is inconvenient in manually adjusting lengths of segments of the walking-assist robot to the body size of the walking trainees with assistance of a person who helps perform the gait training is necessary every time.

As the lengths of the segments are manually adjusted, it is difficult to adjust the walking-assist robot to an appropriate set of specific lengths of the walking trainee's body size, thus causing errors in adjustments. In addition, due to individual differences of the assistants who adjust the segment lengths, wearing the walking-assist robot tends to consume remarkably increased time and manpower.

SUMMARY OF THE INVENTION

In order to solve the afore-mentioned problems, an aspect of the present invention may be achieved by providing a robot for gait training and an operating method thereof that are capable of checking an angle, speed and torque of each joint of a walking trainee in real time, comparing the current walking of the walking trainee with the standardized walking pattern appropriate for the training for the walking trainee, and analyzing and determining whether the gait training is correctly performed and what walking pattern is more appropriate for the walking trainee.

In addition, another aspect of the present invention may be achieved by providing a robot for gait training and an operating method thereof that are capable of preventing occurrence of errors due to manual operations and remarkably improving effectiveness of time and manpower by driving a segment length adjustment device of a walking-assist robot and automatically setting the segment length of the walking-assist robot depending on the walking trainee's body size when information about the walking trainee's body size is input.

In order to accomplish the above aspects, the present invention provides a robot for gait training including: a walking-assist robot (100) put on legs of a walking trainee; a treadmill (200) with a conveyor belt floor which moves at a designated speed in order for the walking trainee to continuously perform gait training at a fixed position; a load-hoist (300) for upwardly supporting the body of the walking trainee; and a controller (400) including an input unit (410) for receiving or inputting information or commands about the size of the body of the walking trainee, and about a speed, angle and rotational force of each joint required for training of the walking trainee, an information storage device for selectively storing the information or commands received through the input unit (410) and information generated during a driving process of the walking-assist robot (100), the treadmill (200) and the load hoist (300), a control unit for controlling driving states of the walking-assist robot (100), the treadmill (200) and the load hoist (300) according to the information or commands input through the input unit (410) or transmitted from the information storage device, and a monitor (420) for numerically or graphically displaying the information transmitted from the walking-assist robot (100), the treadmill (200), the load hoist (300) and the information storage device.

Here, the walking-assist robot (100) may include: a position sensor for transmitting a position of each joint of the walking-assist robot (100) to the control unit of the controller (400); and a gear member for receiving a signal from the control unit of the controller (400) and adjusting the position of each joint and lengths of segments of the walking-assist robot (100).

In addition, the walking-assist robot (100) may further include a pressure sensor for transmitting the signal of a contact between a sole of the walking trainee and the treadmill (200) to the control unit of the controller (400).

Further, the load hoist (300) may include: a harness (310) put on the body of the walking trainee with a lower part thereof; a harness driving unit (320) for receiving a signal from the control unit of the controller (400) and having a drive means for adjusting a vertical length of the harness (310); and a load sensor for transmitting the value of a load applied to the harness (310) to the control unit of the controller (400).

Furthermore, the input unit (410) of the controller may include: a main body (411) cased with the information storage device, the monitor (420) and the control unit of the controller (400), and having an input terminal allowing a direct input of information or commands to the information storage device or the control unit of the controller (400); and a remote controller (412) having a wireless input terminal for transmitting the information or commands to the information storage device or the control unit of the controller (400).

In addition, the remote controller (412) may include: a wireless input unit (412*a*) for transmitting an input command of progressing the walking-assist robot (100) in a forward direction or a reverse direction to the information storage device or the control unit of the controller (400) through a touch operation in real time; and a wireless monitor (412*b*) for displaying in real time a progress state of the walking-assist robot (100) in a forward direction or a reverse direction, a hip joint angle, a knee joint angle, an ankle joint angle, and the current time in the designated walking cycle.

Further, the present invention provides an operating method of a robot for gait training including a walking-assist robot (100) put on legs of a walking trainee, a treadmill (200) for providing a conveyor belt floor moving at a designated speed in order for the walking trainee to continuously perform gait training at a fixed position on the treadmill, a load hoist (300) for upwardly supporting the body of the walking trainee, and a controller (400) for receiving and selectively storing information about the size of the body of the walking trainee, and speed, angle and rotational force of each joint required for training of the walking trainee, and numerically or graphically displaying the information and commands, and controlling driving states of the walking-assist robot (100), the treadmill (200) and the load hoist (300). The method includes: an information input step of acquiring the size of the body of the walking trainee, information about a walking pattern obtained through a gait training or a walking test, and information or commands required to drive and set the walking-assist robot (100), the treadmill (200) and the load hoist (300) by transferring them from a server of a network system or an information storage device of the controller (400) or by receiving them through an operation of an input terminal of an input unit (410) of the controller; a robot driving step of driving the walking-assist robot (100), the treadmill (200) and the load hoist (300) in a specific pattern according to the information or commands input in the information input step; a training data generating step of receiving information about speed, angle and torque of each joint of the walking trainee under the gait training in the specific pattern in the robot driving step in real time, and selectively classifying and storing the information inputted in real time in the information storage of the controller; and a training data output step of outputting the information input or stored in the training data generating step on a screen of the a monitor (420) of the controller in real time.

Here, the walking-assist robot (100) may include a position sensor for transmitting a position of each joint of the walking-assist robot (100) to the control unit of the controller (400), and a gear member for adjusting a position of each joint and lengths of segments of the walking-assist robot (100) depending on a gearing state therebetween, and the robot driving step may include: a joint position input step of receiving the position of each joint of the walking-assist robot (100) from the position sensor of the walking-assist robot (100); a segment length calculation step of calculating relative distances between positions of the respective joints input in the joint position input step and obtaining the lengths of the segments of the walking-assist robot (100); a length comparison and calculation step of comparing the lengths of the segments obtained in the segment length calculation step and the size data of the body of the walking trainee input in the information input step and calculating differences therebetween; and a segment length adjustment step of adjusting the driving direction and displacement of the gear member of the walking-assist robot (100) according to the differences obtained in the length comparison and calculation step and locating each joint of the walking-assist robot (100) at the position of each corresponding joint of the walking trainee.

Further, the walking-assist robot (100) may include a pressure sensor for transmitting a signal for contact between a sole of the walking trainee and the treadmill (200) to the control unit of the controller (400), and the robot driving step may include: a contact signal input step of receiving a signal for contact between the sole of the walking trainee and the treadmill (200) from the pressure sensor of the walking-assist robot (100) in real time; a walking speed calculation step of calculating a walking speed of the walking trainee by dividing a stride between two legs by a walking cycle defined by a time difference of the contacts of the two legs with the treadmill (200) during one stride of the walking trainee in real time or periodically; and a both leg speed synchronization step of driving the treadmill at the same speed as the walking speed obtained in the walking speed calculating step.

Furthermore, the walking-assist robot (100) may include a pressure sensor for transmitting a signal for contact between a sole of the walking trainee and the treadmill (200) to the control unit of the controller (400), and the robot driving step may include: a contact signal input step of receiving the contact presence between the sole of the walking trainee and the treadmill (200) from the pressure sensor of the walking-assist robot (100) in real time; a contact time comparison and calculation step of comparing times of one leg of the walking trainee contacting with and separating from the treadmill (200) with reference times predetermined through the information input step, and calculating difference therebetween; and a one leg speed synchronization step of adjusting a driving speed of the treadmill (200) according to the difference obtained in the contact presence comparison and calculation step and driving the treadmill (200) at the same speed as the walking speed of one of the two legs of the walking trainee.

In addition, the load hoist (300) may include a harness (310) put on the body of the walking trainee with a lower part thereof, a harness driving unit (320) having a drive means for adjusting a vertical length of the harness (310), and a load sensor for transmitting the value of a load applied to the harness (310) to the control unit of the controller (400), and the robot driving step may include: a load input step of receiving the value of a load applied to the harness (310) from the load sensor of the load hoist (300) in real time; a load comparison and calculation step of comparing the load inputted in the load input step and a designated hoist level inputted in the information input step and calculating difference therebetween; and a designated hoist level maintaining step of adjusting the driving direction and driving time of the harness driving unit (320) of the load hoist (300) according to the difference obtained in the load comparison and calculation step and adjusting the hoist level of the walking trainee to the designated hoist level by adjusting the length adjustment of the harness (310).

Further, the operating method of a robot for gait training may be separately operated either in a walking test mode or in a gait training mode. In the walking test mode, the robot driving step, the training data generating step and the training data output step are performed in real time during receipt of a progress command of a forward direction or a reverse direction for the walking-assist robot (100) in the information input step, whereas driving of the walking-assist robot (100) is stopped in a state in which the command of the progress direction for the walking-assist robot (100) is not inputted. In the gait training mode, when a command for driving the walking-assist robot (100), the treadmill (200) and the load hoist (300) in a specific pattern is primarily input in the information input step, the robot driving step, the training data generating step and the training data output step are continuously performed according to the command primarily input in the information input step until another command is re-inputted in the information input step.

Here, the walking test mode may be separately operated either in an individual drive mode of individually moving each joint corresponding to the hip joint, knee joint and ankle joint of the walking-assist robot (100); or in a combined drive mode of simultaneously moving the respective joints of the walking-assist robot (100) corresponding to the hip joint, knee joint and ankle joint.

In addition, in the walking test mode, the input unit (410) of the controller may be a remote controller (412) for wirelessly transmitting the information or commands to the information storage device or the control unit of the controller (400).

Further, the remote controller (412) may include: a wireless input unit (412a) for transmitting an input command of progressing the walking-assist robot (100) in a forward direction or a reverse direction to the information storage device or the control unit of the controller (400) through a touch operation in real time; and a wireless monitor (412b) for receiving information about a walking progress state of the walking-assist robot (100) in the forward direction or the reverse direction, the time in the walking cycle, and a hip joint angle, a knee joint angle and an ankle joint angle at the corresponding time, from the information storage device or the control unit of the controller (400) and displaying the information in real time.

Furthermore, in the training data output step, both the information about the angle, speed, rotational force and hoist level of each joint in a standard type appropriate for the walking trainee previously inputted in the information input step and the information about the angle, speed, rotational force, and hoist level of each joint inputted in real time in the training data generating step may be displayed together on one screen.

ADVANTAGEOUS EFFECTS

As can be seen from the foregoing, the angle, speed, torque of each joint and contact state with the conveyor belt floor of the walking trainee can be checked in real time through the monitor of the controller and the wireless monitor of the remote controller. In addition, it is possible to analyze and determine whether the walking trainee correctly performs the gait training and which walking pattern is more appropriate for the walking trainee, by clearly checking and comparing a difference between the standard walking pattern and the currently performed walking and displaying both the standardized walking patterns appropriate for the training for the walking trainee and the current walking on one screen.

Further, by storing and sharing records of patient's body size and training information through a communication network that enables transmission of information between the information storage device of the controller and a plurality of controllers, even when the patient performs the gait training at different times and places, the segment lengths of the walking-assist robot can be automatically adjusted depending on the walking trainee's body size, without re-inputting of the patient's body size or training conditions. Furthermore, it is possible to check information about the training performance and training method of the walking trainee and to maintain consistent treatment through the training with a walking pattern appropriate for the walking trainee on the basis of the information.

In addition, when information of patient ID of a walking trainee, or the walking trainee's body size such as a height, a thigh length, a shank length, and an ankle height is inputted, the segment length adjustment device of the walking-assist robot is automatically driven to adjust the segment lengths of the walking-assist robot depending on the segment lengths of the walking trainee, preventing error occurrences by a manual adjustment of the segment lengths of the walking-assist robot and thus remarkably improving effectiveness of time and manpower.

Further, by calculating a walking speed of a walking trainee from a sensing cycle and a stride of the pressure sensors installed on two legs to synchronize a driving speed of the treadmill to the walking speed of the walking trainee, or by comparing a sensing time and position of the pressure sensor installed at one leg with a preset time and position to synchronize the driving speed of the treadmill to the walking speed of the walking trainee, it is possible to prevent a leg-drag during the gait training and instability of a walking position and to perform stably the gait training in a designated space, regardless of whether the walking trainee wears the walking-assist robot on one leg or both legs.

Furthermore, when a training performance capability of the walking trainee is improved or lowered and requires change or modification of the walking pattern before continuous performance of the gait training according to a specific walking pattern in the gait training mode or during the gait training in the gait training mode, the walking test mode can be operated to independently or synchronously drive the respective joints of the walking-assist robot, in order to check available criteria of the respective joints of the walking trainee and to find a walking pattern most appropriate for the gait training of the walking trainee.

In addition, since a command needed to drive the walking-assist robot can be inputted using the remote controller in real time even at a position distant from the main body of the controller, a therapist can control the walking-assist robot to perform more efficiently the gait training while checking the walking state of the walking trainee from various positions. Further, while the gait training is performed according to a specific walking pattern using the wireless input unit of the remote controller in the walking test mode, a usability limit of each joint of the walking trainee can be clearly found by repeating progress of the robot in the reverse direction and the forward direction at times when the patient feels discomfort or does not wish to progress further and by checking an availability state of each joint through the wireless monitor in real time.

Furthermore, it is possible to receive information or commands required to drive the robot and automatically drive the robot according to the information or commands, display the driving state of the robot along with data of an ideal pattern, and independently or synchronously drive each joint of the robot using the remote controller in the walking test mode to apply various driving patterns on trial, thereby finding out causes of the problems. Thus, the operating method may be variously applied to walking analysis of other bipedal walking robots as well as the walking-assist robot put on a human body.

DESCRIPTION ABOUT NUMERALS USED IN DRAWINGS

| | |
|---|---|
| 100: | Walking-assist robot |
| 200: | Treadmill |
| 300: | Load hoist |
| 310: | Harness |
| 320: | Harness driving unit |
| 400: | Controller |
| 410: | Input unit of the Controller |
| 411: | Main body of the Input unit |
| 412: | Remote controller |
| 412a: | Wireless input unit |
| 412b: | Wireless monitor |
| 420: | Monitor of the Controller |
| 421: | Main Body of the Monitor |

DETAILED DESCRIPTION OF EXEMPLARY EMBODIMENTS

A robot for gait training and an operating method thereof in accordance with the present invention will be described more fully hereinafter with reference to the accompanying drawings, in which embodiments of the invention are shown.

Figure 1:
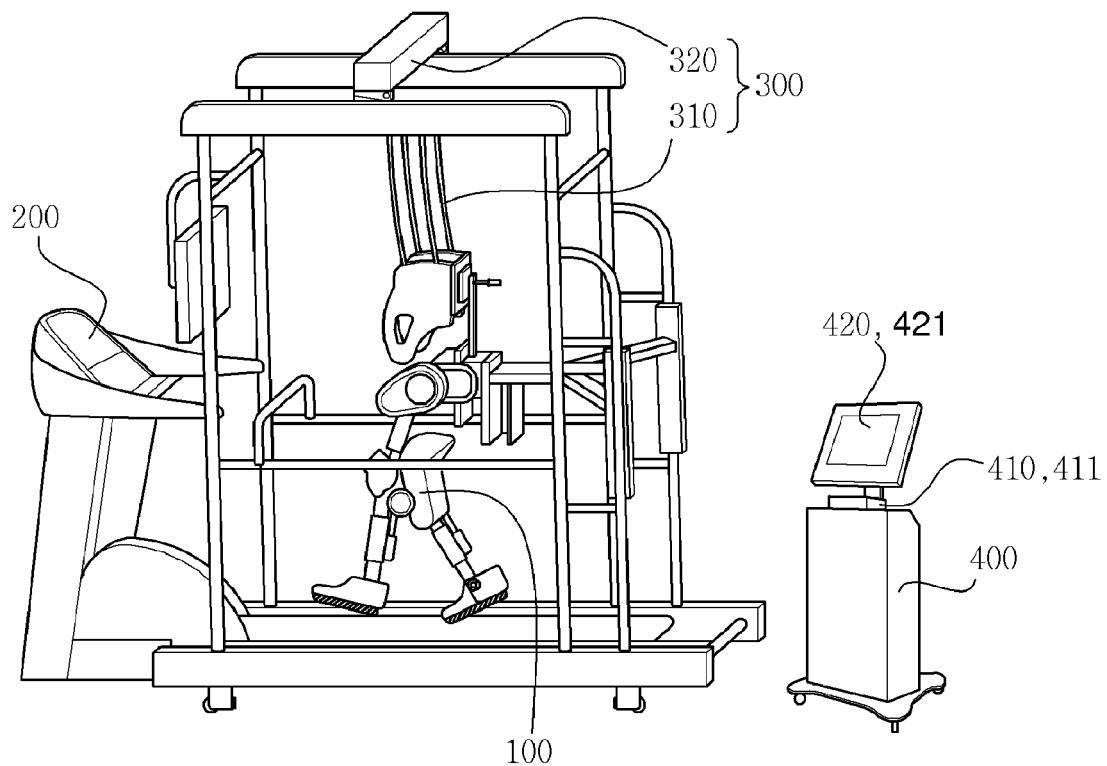
FIG. 1 is a schematic view of a robot for gait training in accordance with a first embodiment of the present invention.
Figure 2:
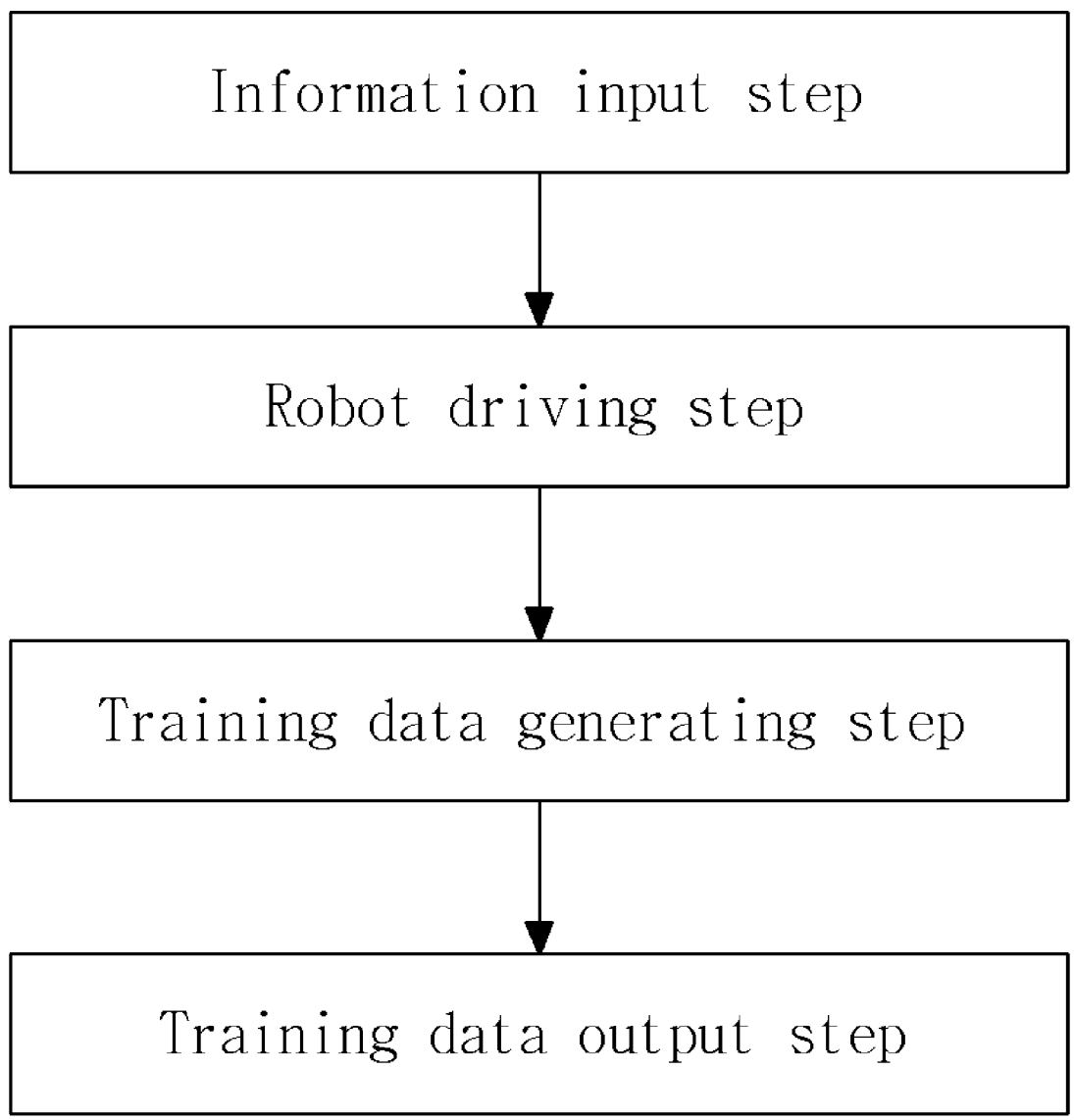
FIG. 2 is a flowchart showing an operating method of a robot for gait training in accordance with the first embodiment of the present invention.
Figure 3:
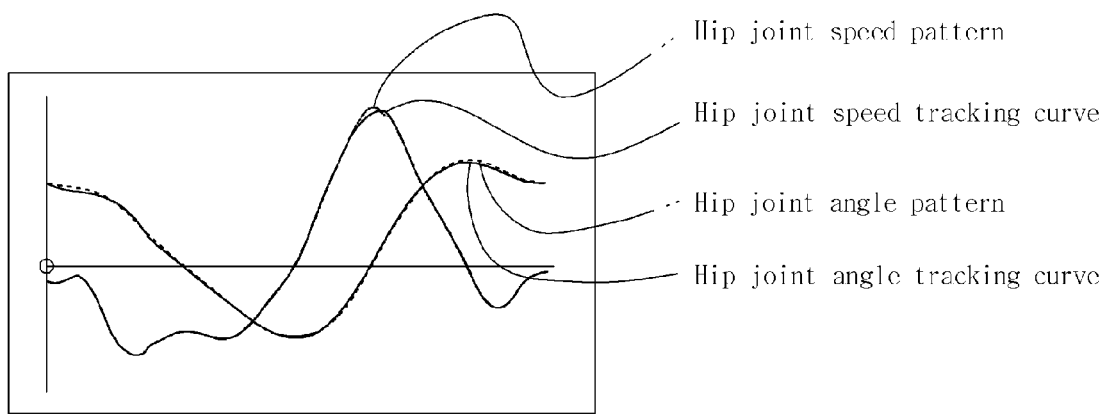
FIG. 3 is a graph of an example of an output displayed on a screen, showing a speed and angle of a hip joint and a speed and angle of a knee joint, which are inputted during training in real time, and pre-input information about a standardized walking pattern appropriate for the training of the walking trainee.
Figure 3:
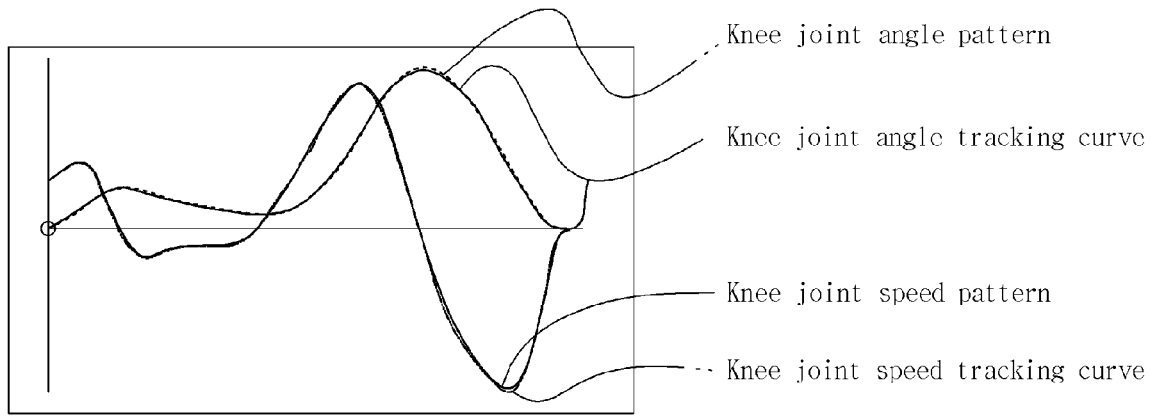

FIG. 1 is a schematic view of a robot for gait training in accordance with a first embodiment of the present invention, FIG. 2 is a flowchart showing an operating method of a robot for gait training in accordance with the first embodiment of the present invention, and FIG. 3 is a graph of an example of an output displayed on a screen, showing a speed and angle of a hip joint and a speed and angle of a knee joint, which are inputted during training in real time, and pre-input information about a standardized walking pattern appropriate for the training of the walking trainee.

Figure 4:
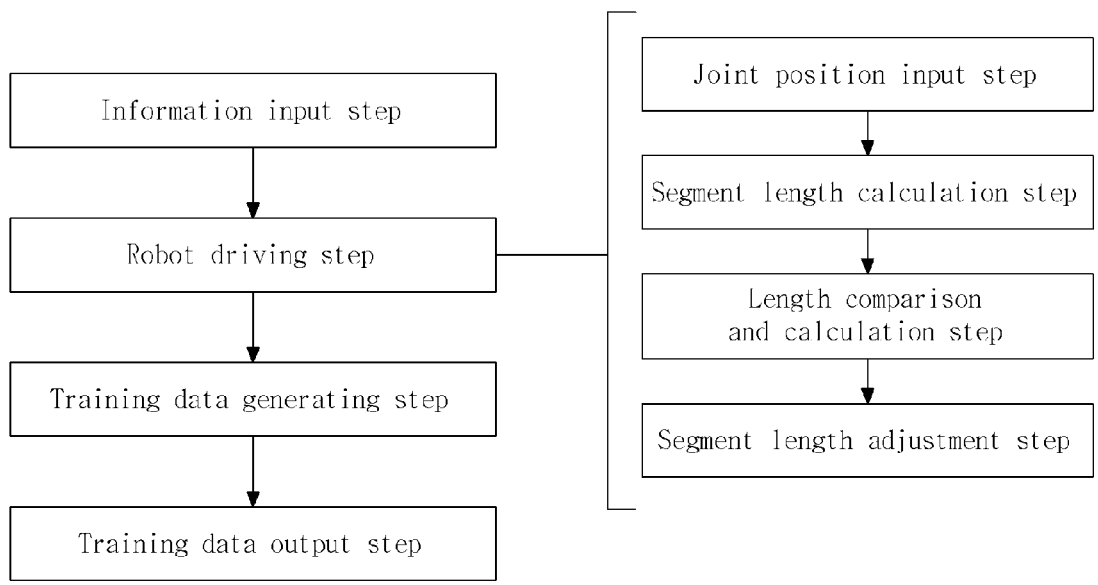
FIG. 4 is a flowchart showing an operating method of a robot for gait training in accordance with a second embodiment of the present invention.
Figure 5:
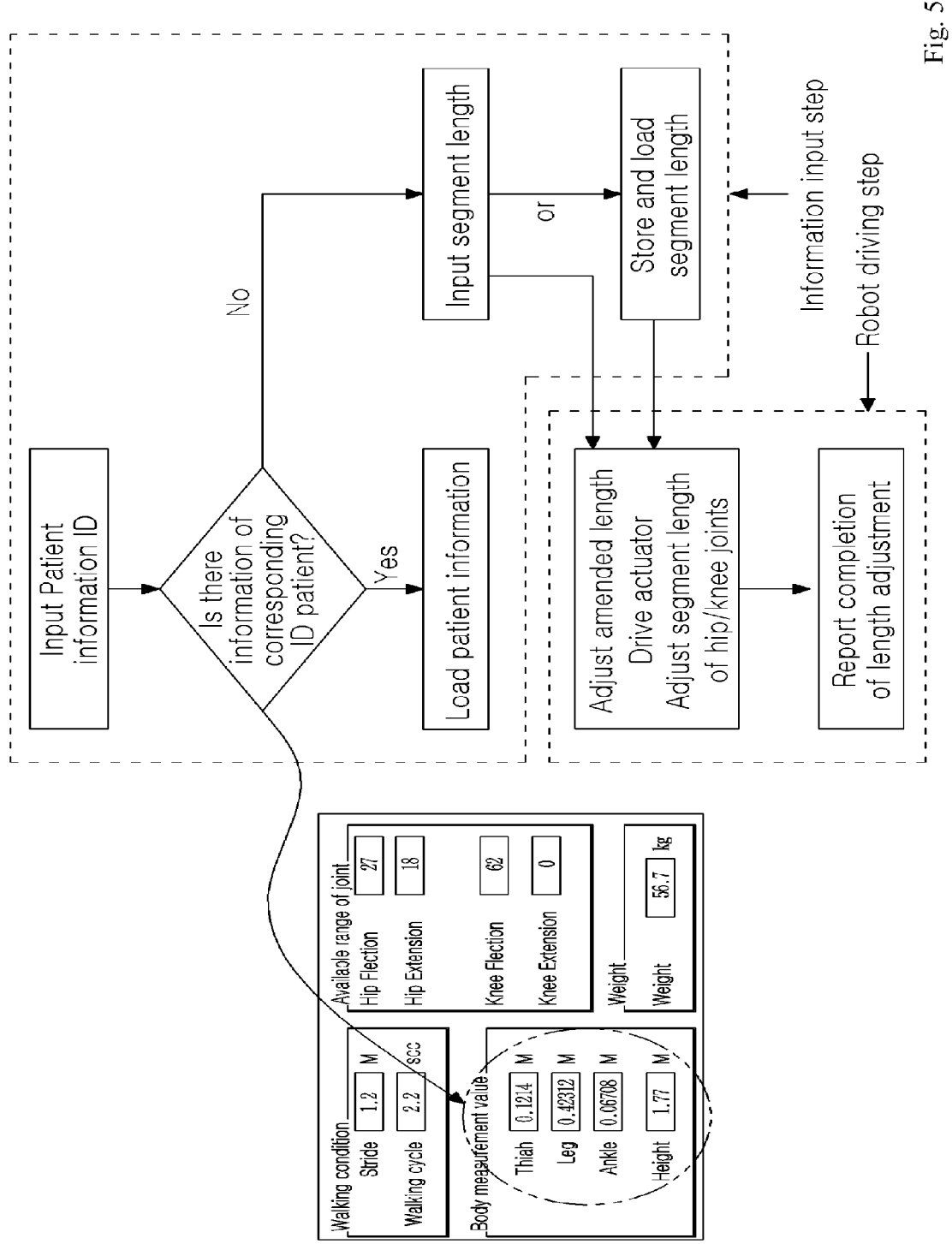
FIG. 5 is a flowchart showing an example of an operating method of automatically adjusting lengths of segments of a walking-assist robot.
Figure 6:
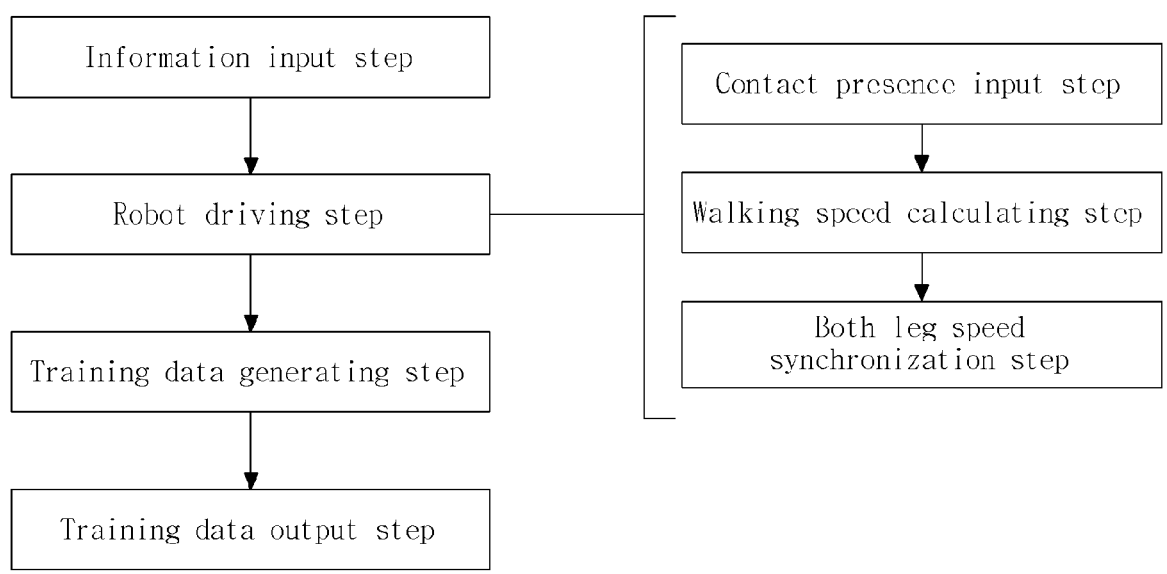
FIG. 6 is a flowchart showing an operating method of a robot for gait training in accordance with a third embodiment of the present invention.
Figure 7:
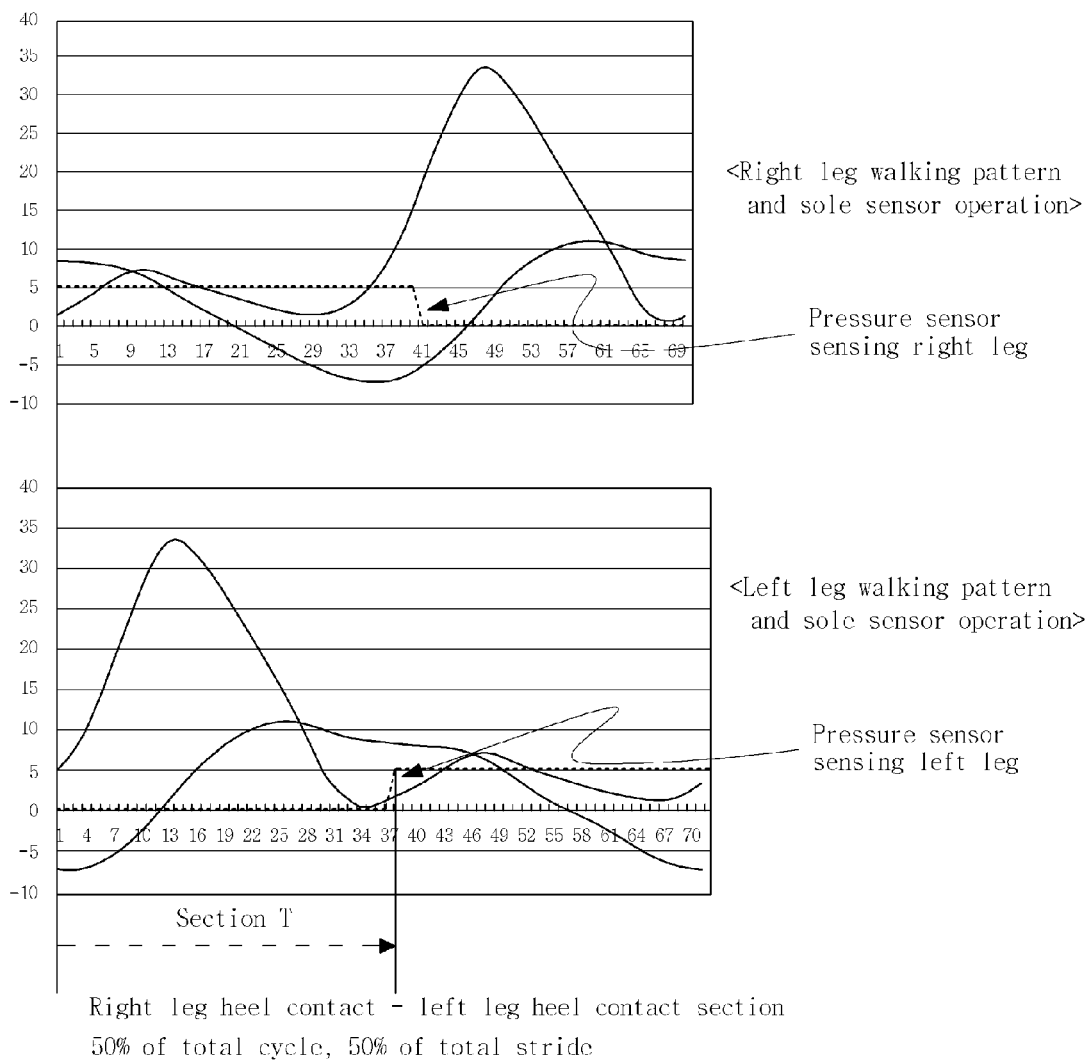
FIG. 7 is a graph showing a relationship between a sensing state of a pressure sensor and a walking cycle and stride.
Figure 8:
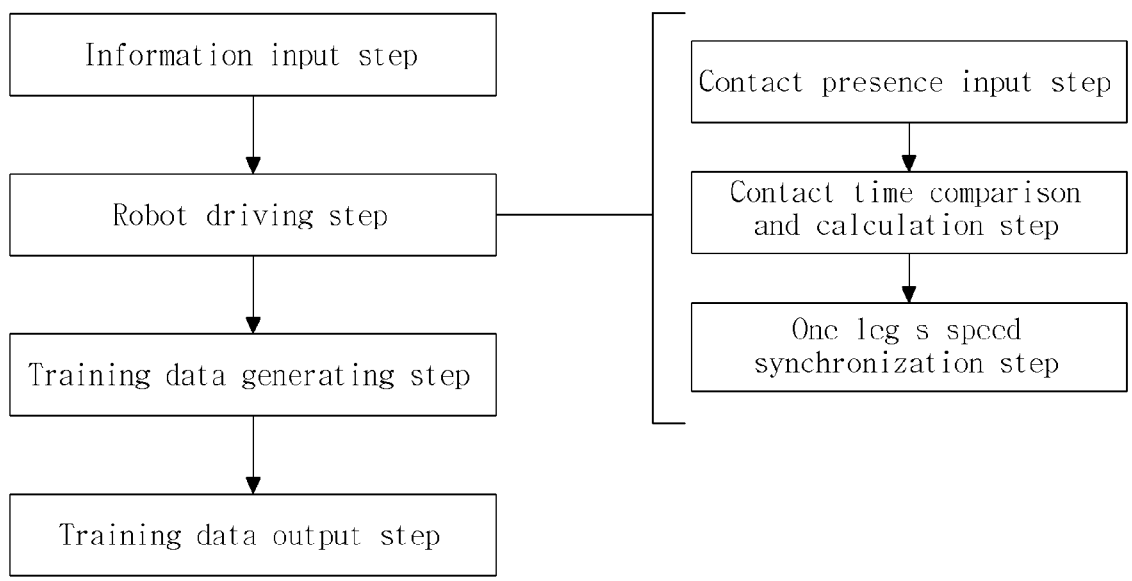
FIG. 8 is a flowchart showing an operating method of a robot for gait training in accordance with a fourth embodiment of the present invention.
Figure 9:
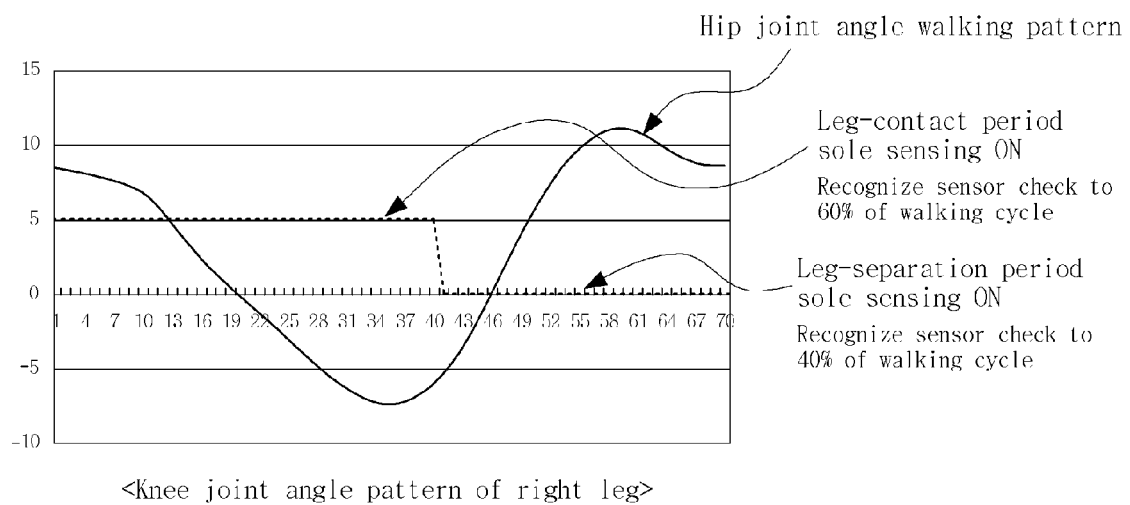
FIG. 9 is a graph showing a real-time sensing state of a pressure sensor according to a standard walking pattern.
Figure 9:
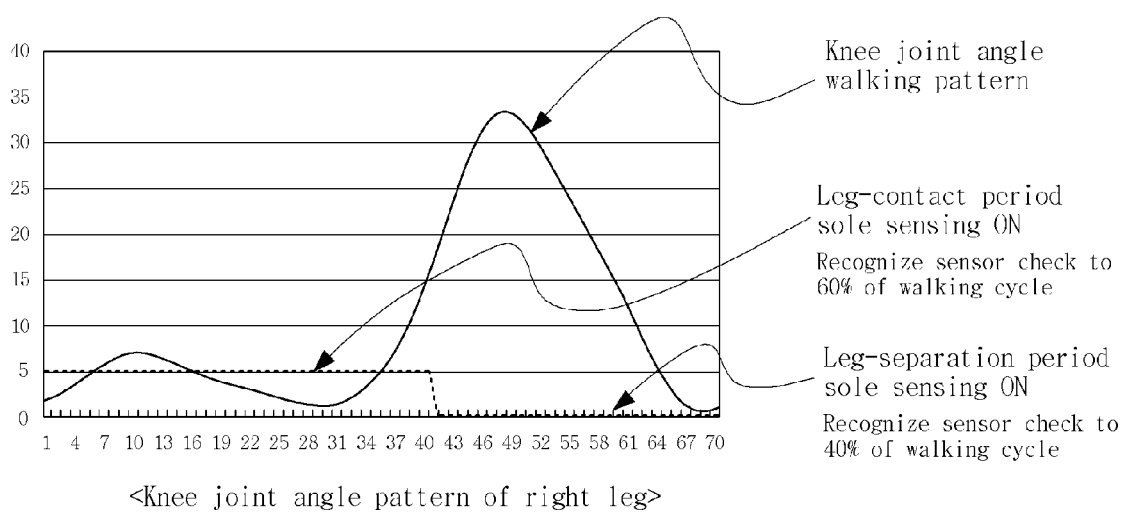
Figure 10:
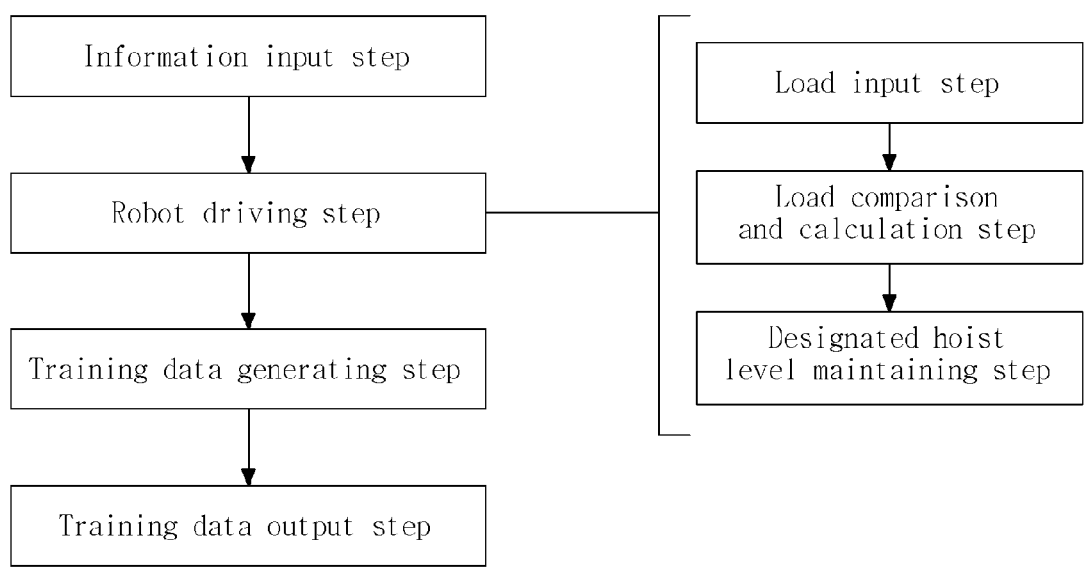
FIG. 10 is a flowchart showing an operating method of a robot for gait training in accordance with a fifth embodiment of the present invention.

In addition, FIG. 4 is a flowchart showing an operating method of a robot for gait training in accordance with a second embodiment of the present invention, FIG. 5 is a flowchart showing an example of an operating method of automatically adjusting lengths of segments of a walking-assist robot, FIG. 6 is a flowchart showing an operating method of a robot for gait training in accordance with a third embodiment of the present invention, FIG. 7 is a graph showing a relationship between a sensing state of a pressure sensor and a walking cycle and stride, FIG. 8 is a flowchart showing an operating method of a robot for gait training in accordance with a fourth embodiment of the present invention, FIG. 9 is a graph showing a real-time sensing state of a pressure sensor according to a standard walking pattern, and FIG. 10 is a flowchart showing an operating method of a robot for gait training in accordance with a fifth embodiment of the present invention.

Figure 11:
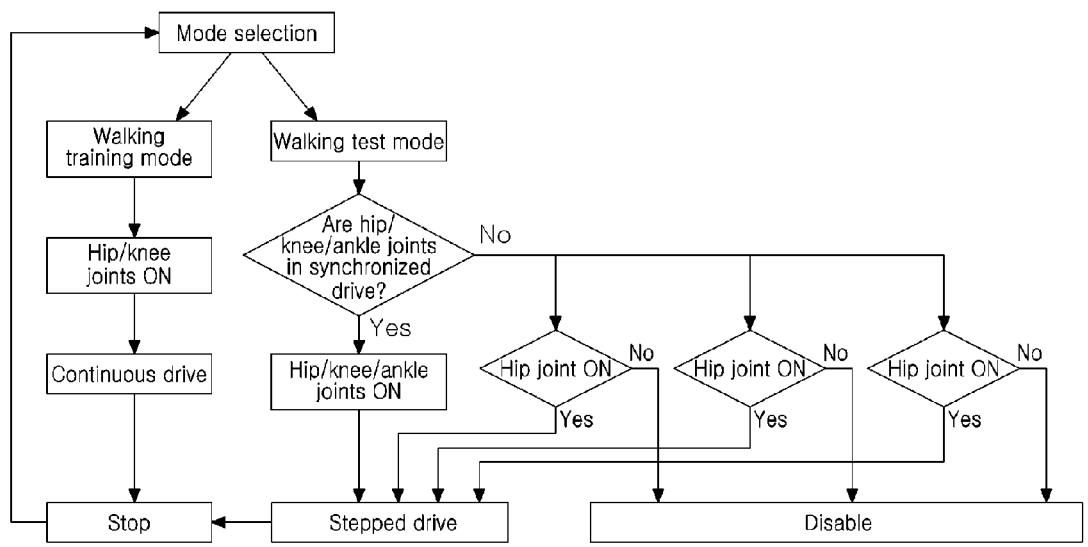
FIG. 11 is a flowchart showing a process of selectively operating a gait training mode and a walking test mode.
Figure 12:
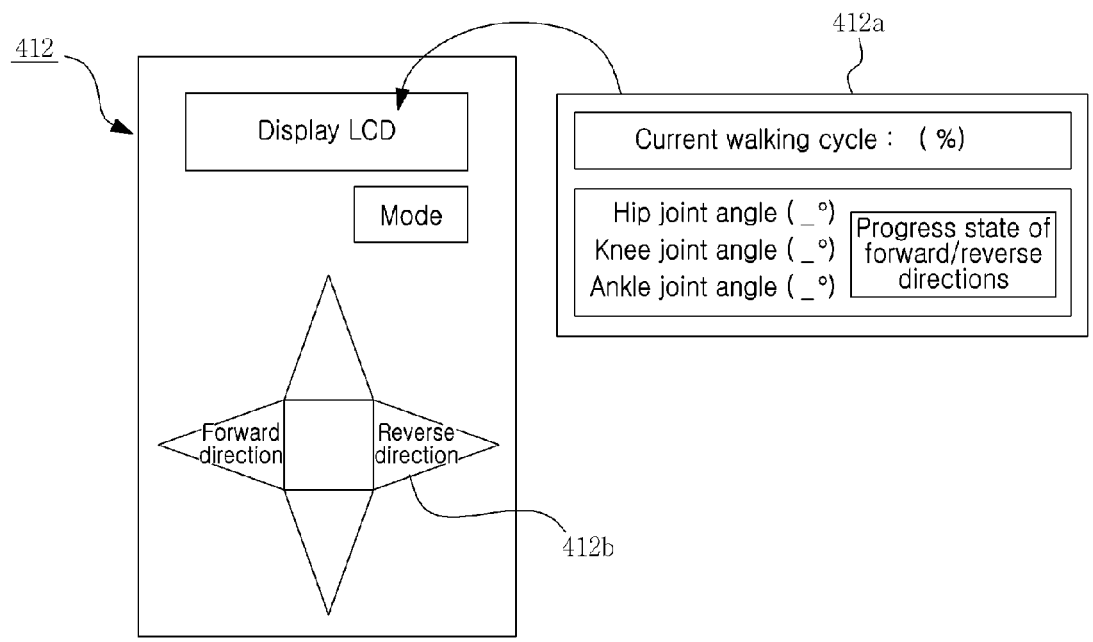
FIG. 12 is a schematic view showing an example of a remote controller.
Figure 13:
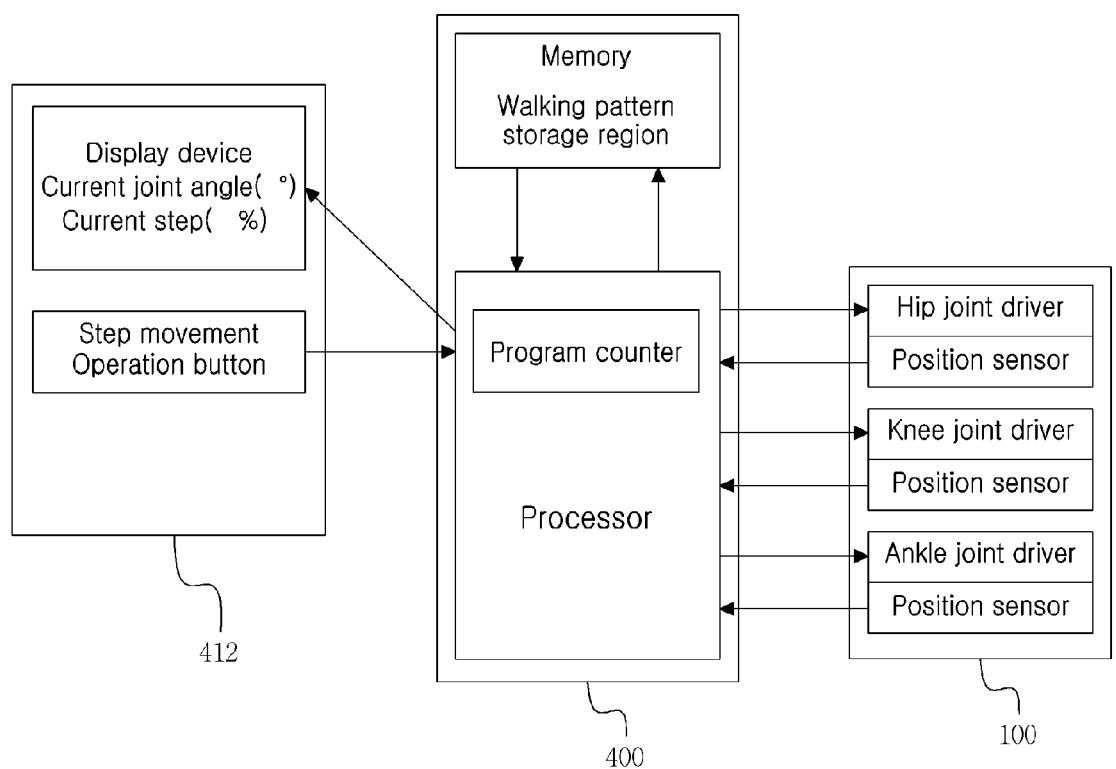
FIG. 13 is a block diagram showing an information and signal transmission relationship between a remote controller, a controller, and a walking-assist robot in a walking test mode.
Figure 14:
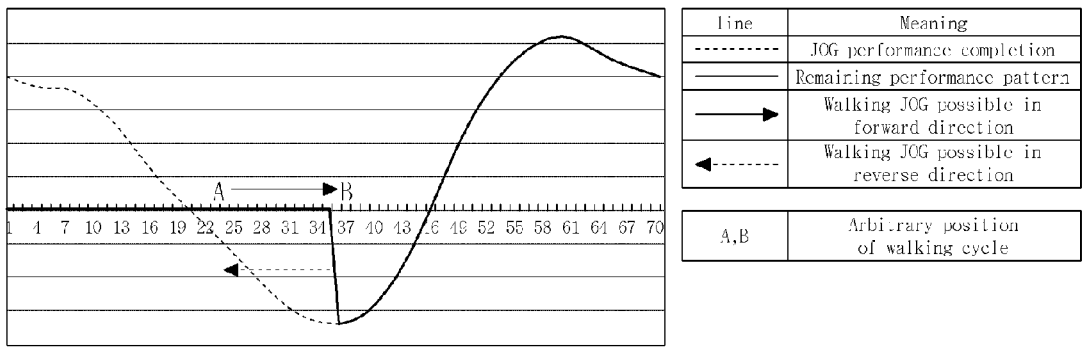
FIG. 14 is a graph showing a process of finding a critical point of usability of the walking trainee's joints by repeating an operation in which the respective joints of the walking-assist robot are individually driven in a forward direction and changed to be driven in a reverse direction at an arbitrary position according to a tracking walking pattern preset in a walking test mode.
Figure 14:
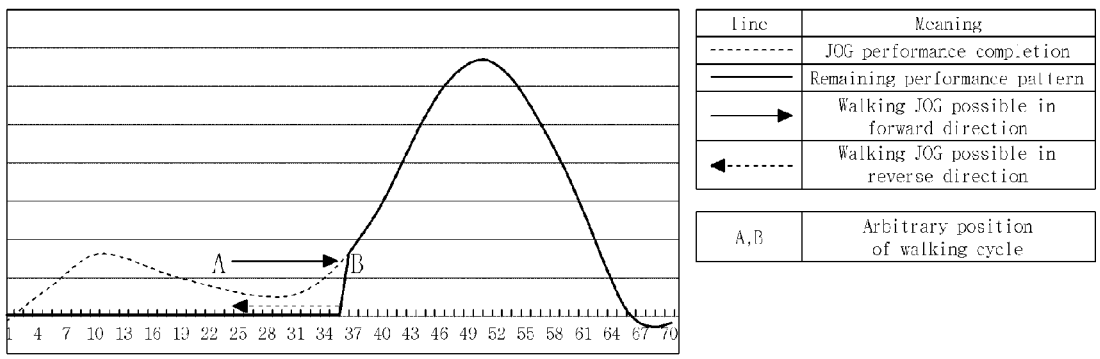
Figure 14:
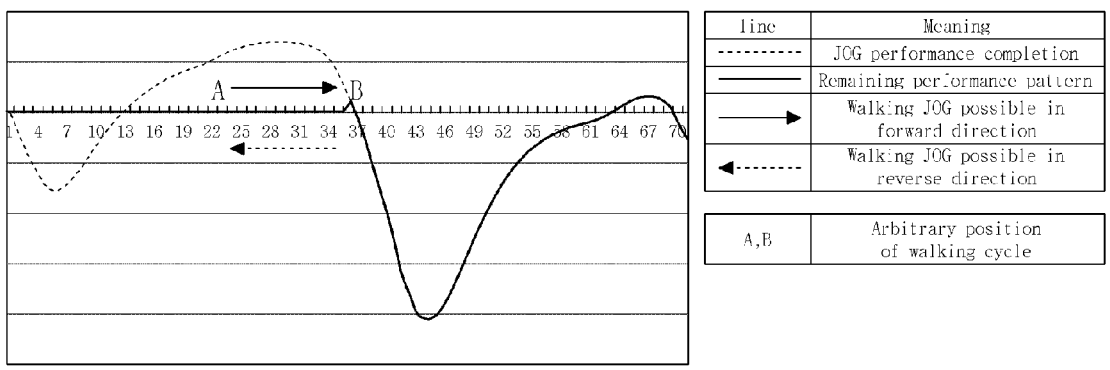
Figure 15:
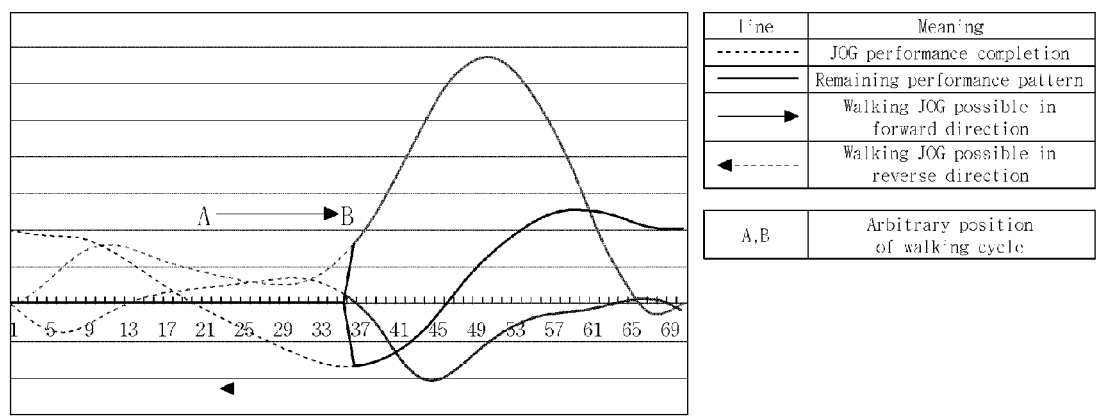
FIG. 15 is a graph showing a process of finding a critical point of usability of the walking trainee's joints by repeating an operation in which all joints of the walking-assist robot are synchronously driven in a forward direction and changed to be driven in a reverse direction at an arbitrary position according to a tracking walking pattern preset in a walking test mode.
Figure 16:
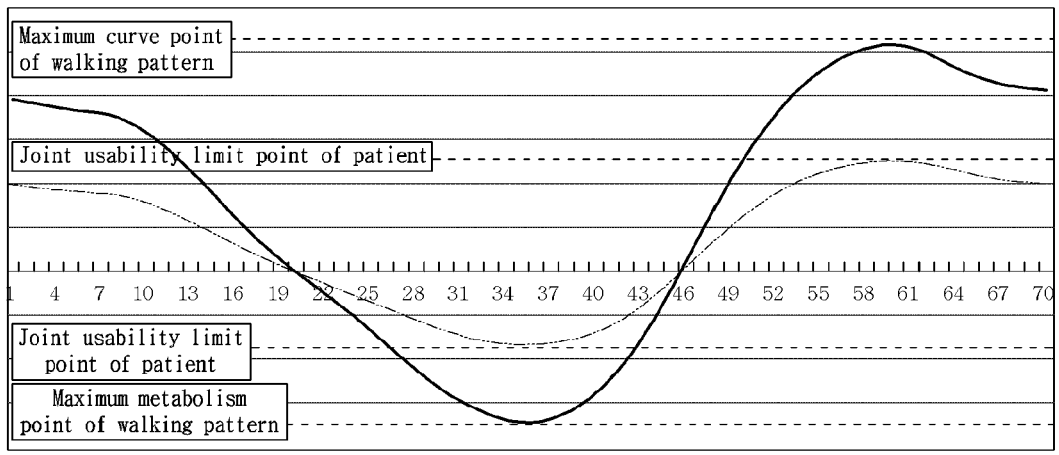
FIG. 16 is a graph showing a walking pattern reconstructed using a critical point of joint usability of the walking trainee.
Figure 16:
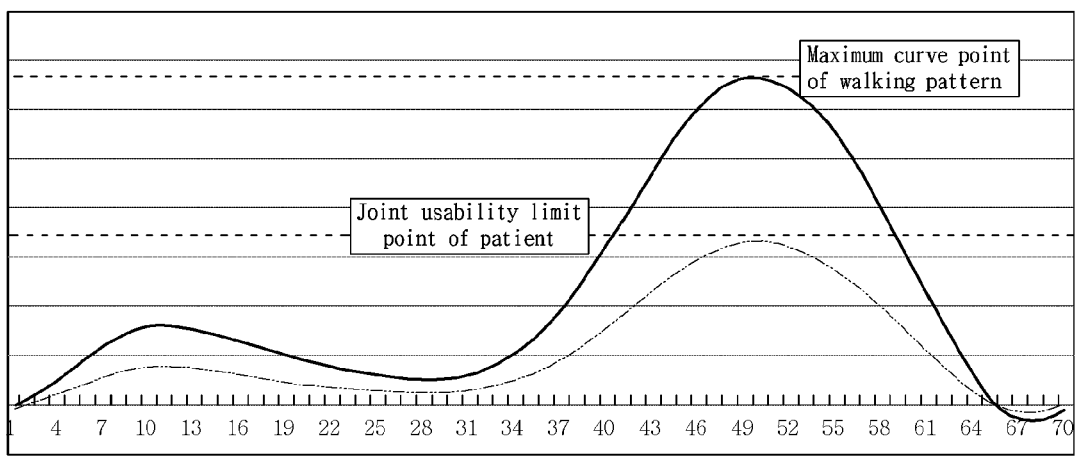
Figure 16:
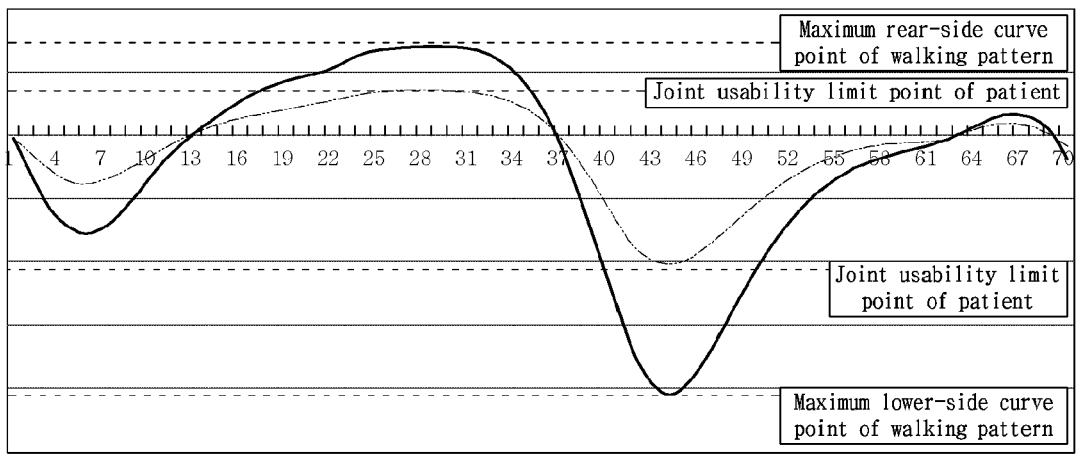

Further, FIG. 11 is a flowchart showing a process of selectively operating in a gait training mode and in a walking test mode, FIG. 12 is a schematic view showing an example of a remote controller, FIG. 13 is a block diagram showing an information and signal transmission relationship between a remote controller, a controller, and a walking-assist robot in a walking test mode, FIGS. 14 and 15 are graphs showing a process of finding a critical point of usability of the walking trainee's joints by repeating an operation in which the respective joints of the walking-assist robot are individually or synchronously driven in a forward direction and changed to be driven in a reverse direction at an arbitrary position according to a tracking walking pattern preset in a walking test mode, and FIG. 16 is a graph showing a walking pattern reconstructed using a critical point of joint usability of the walking trainee.

As shown in FIG. 1, a robot for gait training in accordance with the present invention includes a walking-assist robot 100, a treadmill 200, a load hoist 300, and a controller 400. The treadmill 200 is driven at a speed corresponding to a walking speed of a walking trainee who wears the walking-assist robot 100 and is in training, and the load hoist 300 upwardly supports the walking trainee's body to a designated hoisting level.

The controller 400 receives information or a command required to drive the walking-assist robot 100, the treadmill 200 and the load hoist 300, controls drive states of the walking-assist robot 100, the treadmill 200 and the load hoist 300 and selectively stores them, and outputs information generated during drive of the walking-assist robot 100, the treadmill 200 and the load hoist 300 and selectively stores them.

The walking-assist robot 100 includes joints corresponding to the walking trainee's joints and put on the legs of the walking trainee who needs the gait training, and has a structure that can adjust positions and angles of joints of the walking-assist robot 100, and lengths of segments formed between the joints. The walking-assist robot 100 may selectively include at least one joint of the hip joints, knee joints and ankle joints, may be put on only one leg, or may be put on both legs depending on necessities of the walking trainee.

The structure and operating theory of the walking-assist robot 100 are known in the art of manufacturing a robot including joints corresponding to legs of a human body and driven in specific patterns, and thus detailed descriptions thereof are omitted. The walking-assist robot is not limited to a specific structure and shape, but may have an appropriate structure selectively applied depending on a disability level and a training state of the walking trainee, a place at which the robot is used, and so on.

The structure and operating theory of the treadmill 200 providing a conveyor belt floor moving at a designated speed so that the walking trainee can continuously perform the gait training in a fixed position are also known in the art, and thus detailed descriptions thereof are omitted. The structure and operating theory of the load hoist 300 for upwardly supporting the walking trainee's body are disclosed in Korean Patent Application No. 2008-21889, entitled "Load-cell Detection Mechanism, Support Frame for Walking-assist Robot and Hoist for Walking-assist Robot including the same" (Korean published application 10-2009-096828, published on 16 Sep. 2009), and thus detailed descriptions thereof are also omitted.

The controller 400 generally includes an input unit 410, an information storage device (not shown), a control unit (not shown), and a monitor 420.

The input part 410 of the controller 400 includes a communication terminal connected to a communication network that enables transmission of information from the control unit or the information storage device of the controller 400 or between a plurality of controllers 400 installed in different places (for example, different hospitals or physical therapy rooms) to receive information or commands about the walking trainee's body size, and a speed, angle and rotational force of each joint needed for the training for a walking trainee from another controller 400 or a network server, or includes a terminal that can input numbers, etc., into the controller 400 to directly receive information or commands from a user.

The input unit 410 of the controller 400 includes a main body 411 cased with the information storage device, the control unit, and the monitor 420 of the controller 400 to maintain a state installed at a fixed position, and providing an input terminal capable of allowing a user to directly input information and commands into the information storage device or the control unit of the controller 400, and a wireless input unit 412b installed at a remote controller 412 (See FIG. 12) disposed at an arbitrary position distant from the main body 411, and transmitting information or commands to the information storage device or the control unit of the controller 400.

The information storage device of the controller 400 selectively classifies and stores information or commands received through the input unit 410 or the control unit, and information generated during a driving process of the walking-assist robot 100, the treadmill 200 and the load hoist 300, and the control unit of the controller 400 controls driving states of the walking-assist robot 100, the treadmill 200 and the load hoist 300 according to information or commands received through the input unit 410 or transmitted from the information storage device of the controller.

The monitor 420 of the controller numerically or graphically displays information or commands received through the input unit 410, driving states of the information storage device, the walking-assist robot 100, the treadmill 200 and the load hoist 300 under control of the control unit, information or commands stored in the information storage device during the gait training, and information transmitted from the information storage device, the walking-assist robot 100, the treadmill 200 and the load hoist 300.

Similarly to the input unit 410 of the controller, the monitor 420 of the controller also includes a main body 421 cased with the information storage device and the control unit of the controller 400 and the main body 411 of the input unit to maintain a state installed at a fixed position, and a wireless monitor 412a of the remote controller disposed at an arbitrary position distant from the main body 421 of the monitor, and receiving and displaying information or commands from the input unit 410, the information storage device or the control unit of the controller in a wireless manner.

Since the commands required to drive the walking-assist robot 100 can be inputted in real time even at a position distant from the main body of the controller 400 using the remote controller 412, a therapist can control the walking-assist robot 100 to more effectively perform the gait training while specifically checking a walking state of the walking trainee at various positions.

An operation method of a robot for gait training in accordance with the present invention relates to a method of operating a robot for gait training as explained above, and, as shown in FIG. 2, generally includes an information input step, a robot driving step, a training data generating step, and a training data output step. In the robot driving step, the walking-assist robot 100, the treadmill 200 and the load hoist 300 are specifically driven according to information received in the information input step. In the training data generating step, information about the respective driving states from the walking-assist robot 100, the treadmill 200 and the load hoist 300 while driving are received and selectively stored. In the training data output step, information generated in the training data generating step is output on a screen.

In the information input step, the walking trainee's body size, information about a walking pattern acquired by the gait training or the test, and information or commands needed to drive and set the walking-assist robot 100, the treadmill 200 and the load hoist 300 are transmitted from a server of a network system or the information storage device of the controller 400, or inputted by operating an input terminal of the input unit 410 of the controller.

In the robot driving step, the walking-assist robot 100, the treadmill 200 and the load hoist 300 are specifically driven according to the information or commands input in the information input step, and information about a walking state of the walking or a driving state of the device trainee at this time is received from detection terminals installed at the walking-assist robot 100 and the load hoist 300 in real time to control and drive the walking-assist robot 100, the treadmill 200 and the load hoist 300 according to the walking state of the walking trainee in a mutual relationship.

In the training data generating step, both information about a speed, angle and torque of each joint of the walking trainee who performs the gait training according to a specific pattern in the robot driving step and information about the respective drive states are received from the walking-assist robot 100, the treadmill 200 and the load hoist 300 in real time, and the information input in real time is selectively classified, arranged and stored in the information storage device of the controller.

In the training data output step, the information inputted or stored in the training data generating step is output on a screen in real time through the main body 421 of the monitor of the controller or the wireless monitor 412a in an appropriate types of numbers, tables, graphs, and figures so that the walking trainee and a therapist can check the angle, speed, torque and floor contact state of each joint of the walking trainee during a gait training.

As shown in FIG. 3, when the information about the angle, speed, rotational force and hoisting level of each joint inputted in real time in the training data generating step is output on a screen with the pre-input information about the angle, speed, rotational force and hoisting level of a standard type appropriate for the walking trainee in the information input step, the walking trainee and the therapist can check and compare the standard walking pattern appropriate for the walking trainee and the currently performed walking on the basis of objective indices, and analyze and determine whether the walking trainee correctly performs the gait training and what walking pattern is more appropriate for the walking trainer.

In operating the robot for gait training as explained above, since the walking-assist robot 100 has a structure including a position sensor (not shown) for transmitting a position of each joint of the walking-assist robot 100 to the control unit of the controller 400 and a gear member (not shown) for receiving a signal from the control unit of the controller 400 to adjust the position of each joint and the lengths of the segments of the walking-assist robot 100, in the robot driving step, as shown in FIG. 4, the lengths of the segments of the walking-assist robot 100 can be automatically adjusted according to the walking trainee's body size by a joint position input step, a segment length calculation step, a length comparison and calculation step, and a segment length adjustment step.

In the joint position input step, the position of each joint of the walking-assist robot 100 is inputted from the position sensor of the walking-assist robot 100. In the segment length calculation step, a relative distance between position data of the respective joints inputted in the joint position input step is calculated to obtain the lengths of the segments of the walking-assist robot 100.

In the length comparison and calculation step, the length of the segment obtained in the segment length calculation step is compared with the walking trainee's body size inputted in the information input step to calculate a difference therebetween. In the segment length adjustment step, a driving direction and displacement of the gear member of the walking-assist robot 100 are adjusted according to the difference obtained in the length comparison and calculating step to locate each joint of the walking-assist robot 100 at a position corresponding to each joint of the walking trainee.

As shown in FIG. 5, when identification (ID) of the walking trainee is inputted and a stored record of the corresponding ID exists, the stored record of the ID is called in. When the ID does not exist or the stored record of the ID does not exist, information about the walking trainee's body size such as a height, a thigh length, a shank length, and an ankle height of the walking trainee is directly inputted. Then, the gear member for adjusting the segment lengths of the walking-assist robot 100 is automatically driven under control of the controller 400 to adjust the segment lengths of the walking-assist robot 100 to the segment lengths of the walking trainee, preventing error occurrence caused by manual adjustment of the segment lengths of the conventional walking-assist robot and thus remarkably improving effectiveness of time and manpower.

In the information input step, by using a communication network that allows transmission of information between the information storage device of the controller 400 and a plurality of controllers 400, when the walking trainee performs the gait training at different times and places, required information can be called from the information storage device of the controller 400, the server connected to the communication network, or another controller 400 to be used for the gait training, without re-input of the patient's body size or training condition every time. As a result, the segment length of the walking-assist robot can be automatically adjusted according to the walking trainee's body size by only inputting the walking trainee's ID, information about training achievement and a training method of the walking trainee can be checked, and the training in a walking pattern appropriate for the walking trainee can performed on the basis of the information, maintaining a consistent treatment.

In operating the robot for gait training in accordance with the present invention as explained above, since the walking-assist robot 100 has a structure including a pressure sensor (not shown) for transmitting presence of a contact between the walking trainee's sole and the treadmill 200 to the control unit of the controller 400, the walking speed of the walking trainee and the conveyor belt driving speed of the treadmill 200 can be automatically synchronized through a contact signal input step, a walking speed calculation step, and a two leg speed synchronization step in the robot driving step as shown in FIG. 6 or through a contact signal input step, a contact time comparison and calculation step, and a one leg speed synchronization step as shown in FIG. 8.

As shown in FIG. 6, the robot driving step includes a sequence of the contact signal input step, the walking speed calculation step and the two leg speed synchronization step. In the contact signal input step, a signal for contact between the walking trainee's sole and the treadmill 200 is inputted from the pressure sensor of the walking-assist robot 100 in real time. In the walking speed calculation step, a walking cycle is determined by the time difference when each two legs of the walking trainee contacts the treadmill 200 in one step, and a stride between two legs is divided by the walking cycle to obtain the walking speed of the walking trainee in real time or periodically. In the two leg speed synchronization step, the treadmill 200 is driven at the same speed as the walking speed obtained in the walking speed calculation step.

FIG. 7 shows that, in the sequential steps of the contact presence input step, the walking speed calculation step, and the both leg speed synchronization step, a difference between sensing times of the right and left legs and a positional difference between the right and left legs (section T) during one stride correspond to 50% of the entire walking cycle and the stride. The treadmill 200 is driven at a speed in which the stride corresponding to the section T is divided by the walking cycle corresponding to the section T, and synchronized to the walking speed of the walking trainee.

In a state in which the gait training is performed in a certain pattern with the walking-assist robot 100 put on both legs, the contact on the treadmill 200 of both legs can be sensed to synchronize the driving speed of the treadmill 200. As the walking speed of one stride is used as a calculation basis, the speed of the treadmill 200 may be synchronized at each stride, or the walking speed of two or more strides may be calculated to synchronize the speed of the treadmill 200 every two strides, i.e., every walking cycle.

As shown in FIG. 8, the robot driving step includes a contact signal input step, a contact time comparison and calculation step, and a one leg speed synchronization step, which are sequentially performed. In the contact signal input step, signals of contact between the walking trainee's both legs and the treadmill 200 are inputted from the pressure sensor of the walking-assist robot 100 in real time. In the contact time comparison and calculation step, contact and separation times of one of the walking trainee's legs from the treadmill 200 is compared with a reference times predetermined through the information input step to calculate a difference therebetween. In the one leg speed synchronization step, the driving speed of the treadmill 200 is adjusted according to the difference obtained in the contact time comparison and calculation step to drive the treadmill 200 at the same speed as the walking speed of one of the walking trainee's both legs.

In the sequential steps of the contact presence input step, the contact time comparison and calculation step, and the one leg speed synchronization step, FIG. 9 shows a reference time previously inputted and designated through the information input step and used as a reference in comparing with the current sensing time and position in the contact time comparison and calculation step. A leg-contact period, which refers to a state in which the leg is in contact with the ground, is generally 60% of the total walking cycle in normal walking, and a leg-separation period, which refers to a state in which the leg is spaced apart from the ground, is generally 40% of the total walking cycle in normal walking. On the basis of the above, FIG. 9 shows appropriate sensing ON/OFF time of the leg-contact period and the leg-separation period on a walking pattern (a hip joint angle walking pattern and a knee joint angle walking pattern shown in FIG. 9) standardized to training for the walking trainee.

Therefore, the reference time compared with the current walking in the contact time comparison and calculation step is a time that the sensing state of the pressure sensor is shifted in a pattern as shown in FIG. 9. When the pressure state is shifted to a shorter time or a farther distance in comparison with the reference time and position, a speed of the treadmill 200 becomes faster than the current driving speed in proportion to the difference, and when the pressure state is shifted to a longer time or a shorter distance, the speed of the treadmill 200 becomes slower than the current driving speed, synchronizing the speed of the treadmill 200 to the walking speed of the walking trainee.

In a state in which the walking trainee wears the walking-assist robot 100 and performs the gait training on only one leg because only one leg requires the gait training, since a moving speed of a normal leg with no robot, which has a variable speed, must be considered as a major factor to avoid an immoderate walking, the speed of the treadmill 200 is preferably synchronized to the walking speed through the contact time comparison and calculation step and the one leg speed synchronization step as explained above.

As described above, the driving speed of the treadmill 200 can be synchronized to the walking speed of the walking trainee by calculating a walking speed using a sensing cycle of the pressure sensor installed at the walking trainee's legs and a stride, or by comparing a sensing time and position of the pressure sensor installed at one leg with a preset arbitrary time and position. Therefore, it is possible to prevent instability of walking due to a leg-drag during the gait training or a relative position difference to the conveyor belt floor, and thus, it is possible for the walking trainee to perform the gait training stably in a designated space, regardless of the number and position of the walking-assist robots put on the walking trainee.

In operating the robot for gait training in accordance with the present invention as explained above, since the load hoist 300 includes a harness 310 put on the walking trainee's body with its lower part, a harness driving unit 320 having a drive means for adjusting a vertical length of the harness 310 using the control unit of the controller 400, and a load sensor for transmitting the value of a load applied to the harness to the control unit of the controller 400, it is possible in the robot driving step to hoist the walking trainee who cannot easily perform the gait training with his/her own weight put on his/her legs uniformly throughout a load input step, a load comparison and calculation step and a designated hoist level maintaining step as shown in FIG. 10.

In the load input step, a load applied to the harness 310 is inputted from the load sensor of the load hoist 300 in real time. In the load comparison and calculation step, the load inputted in the load input step is compared with a designated hoist level inputted in the information input step to calculate a difference therebetween. In the designated hoist level maintaining step, a driving direction and a driving time of the harness driving unit 310 of the load hoist 300 are adjusted according to the difference obtained in the load comparison and calculation step such that the hoist level of the walking trainee is adjusted to correspond to the designated hoist level by length adjustment of the harness 310.

In applying an operating method of a robot for gait training in accordance with the present invention as described above, a walking test mode and a gait training mode are applied selectively as shown in FIG. 11.

The walking test mode is an operating mode in which the robot driving step, the training data generating step and the training data output step are performed in real time while a progress command in a forward direction or a reverse direction for the walking-assist robot 100 is inputted in the information input step, whereas driving of the walking-assist robot 100 is stopped in a state in which a command of a progress direction for the walking-assist robot 100 is not inputted.

The walking test mode is an operating mode in which the walking-assist robot can be driven in real time only while a user operates the robot so that the user can rapidly transfer the walking states in real time and inspect appropriateness of each pattern. The walking test mode can be operated either in an individual drive mode in which the respective joints corresponding to the hip joint, the knee joint and the ankle joint of the walking-assist robot 100 are individually moved, or in a combined drive mode in which the respective joints corresponding to the hip joint, the knee joint and the ankle joint of the walking-assist robot 100 are simultaneously moved. As such, it is possible to diagnose the walking tests more precisely and clearly by subdividing the tests into individual tests of respective joints and the combined tests correlating all the related joints together.

In the walking test mode, the input unit 410 of the controller may be the remote controller 412 having a wireless input terminal capable of transmitting information or commands to the information storage device or the control unit of the controller 400 in a wireless manner so that a therapist can control a drive state of the walking-assist robot in real time at various positions where the training state of the walking trainee can be readily checked. Of course, for the gait training mode, the same effect may be accomplished using the remote controller 412.

As shown in FIG. 12, the remote controller 412 may include a wireless input unit 412a for transmitting an input command of progressing the walking-assist robot 100 in a forward direction or a reverse direction to the information storage device or the control unit of the controller 400 through a touch operation in real time, and a wireless monitor 412b for receiving information about a walking progress state of the walking-assist robot 100 in the forward direction or the reverse direction, current time in the walking cycle, and a hip joint angle, a knee joint angle and an ankle joint angle at the corresponding time, from the information storage device or the control unit of the controller 400, and for displaying the information in real time.

FIG. 13 is a block diagram showing an information and signal transmission relationship between the remote controller 412, the controller 400 and the walking-assist robot 100. A walking trainee or a therapist can input a forward direction progress command into the controller 400 through the wireless input unit 412*a* of the remote controller to individually or combinedly drive the respective joints of the hip joint, the knee joint and the ankle joint of the walking-assist robot 100, so that the position information of each joint can be received from the position sensor to be selectively stored and information about times in the entire walking cycle and positions of the respective joints can be checked through the wireless monitor 412*b* of the remote controller.

The gait training mode is an operating mode in which the robot driving step, the training data generating step and the training data output step are continuously performed according to a command primarily inputted in the information input step until another command is re-input in the information input step, when the command for driving the walking-assist robot 100, the treadmill 200 and the load hoist 300 in a specific pattern is primarily input in the information input step. That is a general gait training mode in which a standardized walking pattern appropriate for the training for the walking trainee is applied and tracked to perform continuous gait training.

In the case where the walking test mode and the gait training mode are selectively operated as described above, when a training performance ability of the walking trainee is improved or lowered and requires change or modification of the walking pattern before continuous performance of the gait training according to a specific walking pattern in the gait training mode or during the gait training in the gait training mode, the walking test mode is operated to independently or synchronously drive the respective joints of the walking-assist robot 100, checking available criteria of the respective joints of the walking trainee and finding out a walking pattern appropriate for the gait training of the walking trainee. Therefore, the appropriate walking pattern found out in the walking test mode can be applied to the gait training mode to perform the actual gait training.

A method of finding out a walking pattern appropriate for the gait training of the walking trainee in the walking test mode is described in more detail. In a state in which an input terminal of the wireless input unit 412 of the remote controller 412 that represents a forward direction is pushed by a finger of an operator, the respective joints of the walking-assist robot 100 are driven in the forward direction according to the specific walking pattern as shown in FIGS. 14 and 15. If a patient feels discomfort or does not wish to progress further, the operator instantly removes the finger from the wireless input unit 412*b* of the remote controller to stop the progress, and then pushes an input terminal of the wireless input unit 412*b* of the remote controller representing a reverse direction to reversely progress the robot until the patient is relieved from the discomfort, and then, progress the robot by a short section in the forward direction. By repeating the above steps, it is possible to find usability limits of the walking trainee's joints.

By finding the walking pattern appropriate for the gait training of the walking trainee using the above method, it is possible to check and store the moving state of each joint through the wireless monitor 412*a* of the remote controller 412 and a main body 421 of the monitor in real time, analyze the training more clearly by objective indices. In applying the gait training mode, it is possible to apply a reconstructed walking pattern to effectively perform the gait training within a range not exceeding the usability limit of the walking trainee's joints, as shown in FIG. 16.

According to the operating method of a robot for gait training in accordance with the present invention, it is possible to receive information or commands required to drive the robot and automatically drive the robot according to the information or commands, display the driving state of the robot with data of an ideal pattern, and independently or synchronously drive each joint of the robot using the remote controller in the walking test mode to apply various driving patterns, thereby finding out causes of the problems. Thus, the operating method may be variously applied to walking analysis of other bipedal walking robots as well as the walking-assist robot 100.

It will be apparent to those skilled in the art that various modifications and variations can be made in the present invention without departing from the spirit or scope of the invention. Thus, it is intended that the present invention covers the modifications and variations of this invention provided they come within the scope of the appended claims and their equivalents.

What is claimed is:

1. An operating method of a robot for gait training, the robot comprising a walking-assist robot (100) for putting on the legs of a walking trainee, a treadmill (200) for providing a conveyor belt floor moving at a designated speed in order for the walking trainee to continuously perform gait training at a fixed position, a load hoist (300) for upwardly supporting the body of the walking trainee, and a controller (400) for receiving and selectively storing information about the size of the body of the walking trainee, and speed, angle and rotational force of each joint required for training of the walking trainee, and numerically or graphically displaying the information and commands, and controlling driving states of the walking-assist robot (100), the treadmill (200) and the load hoist (300), the operating method comprising:

an information input step of acquiring the size of the body of the walking trainee, information about a walking pattern obtained through a gait training or a walking test, and information or commands required to drive and set the walking-assist robot (100), the treadmill (200) and the load hoist (300) by transferring them from a server of a network system or an information storage device of the controller (400) or by receiving them through an operation of an input terminal of an input unit (410) of the controller;

a robot driving step of driving the walking-assist robot (100), the treadmill (200) and the load hoist (300) in a specific pattern specified by the information or commands input in the information input step;

a training data generating step of receiving information about speed, angle and torque of each joint of the walking trainee under the gait training in the specific pattern in the robot driving step in real time, and selectively classifying and storing the information inputted in real time in the information storage of the controller; and a training data output step of outputting the information inputted or stored in the training data generating step on a screen of the monitor (420) of the controller in real time;

wherein the walking-assist robot (100) comprises a position sensor for transmitting a position of each joint of the walking-assist robot (100) to the control unit of the controller (400), and a gear member for adjusting a position of each joint and lengths of segments of the walking-assist robot (100) depending on a gearing state therebetween, and the robot driving step comprises:

a joint position input step of receiving the position of each joint of the walking-assist robot (100) from the position sensor of the walking-assist robot (100);

a segment length calculation step of calculating relative distances between positions of the respective joints input in the joint position input step and obtaining the lengths of the segments of the walking-assist robot (100);

a length comparison and calculation step of comparing the lengths of the segments obtained in the segment length calculation step and the size data of the body of the walking trainee inputted in the information input step and calculating differences therebetween; and a segment length adjustment step of adjusting the driving direction and displacement of the gear member of the walking-assist robot (100) according to the differences obtained in the length comparison and calculation step and locating each joint of the walking-assist robot (100) at the position of each corresponding joint of the walking trainee.

2. The operating method according to claim 1, wherein the walking-assist robot (100) comprises a pressure sensor for transmitting a signal for contact between a sole of the walking trainee and the treadmill (200) to the control unit of the controller (400), and the robot driving step comprises:
a contact signal input step of receiving a signal for contact between the sole of the walking trainee and the treadmill (200) from the pressure sensor of the walking-assist robot (100) in real time;

a walking speed calculation step of calculating a walking speed of the walking trainee by dividing a stride between two legs by a walking cycle defined by a time difference of the contacts of the two legs with the treadmill (200) during one stride of the walking trainee in real time or periodically; and a both leg speed synchronization step of driving the treadmill at the same speed as the walking speed obtained in the walking speed calculating step.

3. The operating method according to claim 1, wherein the walking-assist robot (100) comprises a pressure sensor for transmitting a signal for contact between a sole of the walking trainee and the treadmill (200) to the control unit of the controller (400), and the robot driving step comprises:
a contact signal input step of receiving the contact presence between the sole of the walking trainee and the treadmill (200) from the pressure sensor of the walking-assist robot (100) in real time;

a contact time comparison and calculation step of comparing times of one leg of the walking trainee contacting with and separating from the treadmill (200) with reference times predetermined through the information input step, and calculating difference therebetween; and a one leg speed synchronization step of adjusting a driving speed of the treadmill (200) according to the difference obtained in the contact presence comparison and calculation step and driving the treadmill (200) at the same speed as the walking speed of one of the two legs of the walking trainee.

4. The operating method according to claim 1, wherein the load hoist (300) comprises a harness (310) put on the body of the walking trainee with a lower part thereof, a harness driving unit (320) having a drive means for adjusting a vertical length of the harness (310), and a load sensor for transmitting the value of a load applied to the harness (310) to the control unit of the controller (400), and the robot driving step comprises:
a load input step of receiving the value of a load applied to the harness (310) from the load sensor of the load hoist (300) in real time;

a load comparison and calculation step of comparing the load inputted in the load input step and a designated hoist level inputted in the information input step and calculating difference therebetween; and a designated hoist level maintaining step of adjusting the driving direction and driving time of the harness driving unit (320) of the load hoist (300) according to the difference obtained in the load comparison and calculation step and adjusting the hoist level of the walking trainee to the designated hoist level by adjusting the length of the harness (310).

5. An operating method of a robot for gait training, the robot comprising a walking-assist robot (100) for putting on the legs of a walking trainee, a treadmill (200) for providing a conveyor belt floor moving at a designated speed in order for the walking trainee to continuously perform gait training at a fixed position, a load hoist (300) for upwardly supporting the body of the walking trainee, and a controller (400) for receiving and selectively storing information about the size of the body of the walking trainee, and speed, angle and rotational force of each joint required for training of the walking trainee, and numerically or graphically displaying the information and commands, and controlling driving states of the walking-assist robot (100), the treadmill (200) and the load hoist (300), the operating method comprising:

an information input step of acquiring the size of the body of the walking trainee, information about a walking pattern obtained through a gait training or a walking test, and information or commands required to drive and set the walking-assist robot (100), the treadmill (200) and the load hoist (300) by transferring them from a server of a network system or an information storage device of the controller (400) or by receiving them through an operation of an input terminal of an input unit (410) of the controller;

a robot driving step of driving the walking-assist robot (100), the treadmill (200) and the load hoist (300) in a specific pattern specified by the information or commands input in the information input step;

a training data generating step of receiving information about speed, angle and torque of each joint of the walking trainee under the gait training in the specific pattern in the robot driving step in real time, and selectively classifying and storing the information inputted in real time in the information storage of the controller; and a training data output step of outputting the information inputted or stored in the training data generating step on a screen of the monitor (420) of the controller in real time;

wherein the method is selectively operated either in a walking test mode or in a gait training mode, in the walking test mode, the robot driving step, the training data generating step and the training data output step are performed in real time during receipt of a progress command of a forward direction or a reverse direction for the walking-assist robot (100) in the information input step, whereas driving of the walking-assist robot (100) is stopped in a state in which the command of the progress direction for the walking-assist robot (100) is not inputted; and in the gait training mode, when a command for driving the walking-assist robot (100), the treadmill (200) and the load hoist (300) in a specific pattern is primarily input in the information input step, the robot driving step, the training data generating step and the training data output step are continuously performed according to the command primarily inputted in the information input step until another command is re-inputted in the information input step.

6. The operating method according to claim 5, wherein the walking test mode is selectively operated either in an individual drive mode of individually moving each joint corresponding to a hip joint, a knee joint and an ankle joint of the walking-assist robot (100); or
in a combined drive mode of simultaneously moving the respective joints of the walking-assist robot (100) corresponding to the hip joint, knee joint and ankle joint.

7. The operating method according to claim 5, wherein, in the walking test mode, the input unit (410) of the controller is a remote controller (412) for wirelessly transmitting the information or commands to the information storage device or the control unit of the controller (400).

8. The operating method according to claim 7, wherein the remote controller (412) comprises:
a wireless input unit (412a) for transmitting an input command of progressing the walking-assist robot (100) in a forward direction or a reverse direction to the information storage device or the control unit of the controller (400) through a touch operation in real time; and
a wireless monitor (412b) for receiving information about a walking progress state of the walking-assist robot (100) in the forward direction or the reverse direction, the time in the walking cycle, and a hip joint angle, a knee joint angle and an ankle joint angle at the corresponding time, from the information storage device or the control unit of the controller (400) and displaying the information in real time.

9. An operating method of a robot for gait training, the robot comprising a walking-assist robot (100) for putting on the legs of a walking trainee, a treadmill (200) for providing a conveyor belt floor moving at a designated speed in order for the walking trainee to continuously perform gait training at a fixed position, a load hoist (300) for upwardly supporting the body of the walking trainee, and a controller (400) for receiving and selectively storing information about the size of the body of the walking trainee, and speed, angle and rotational force of each joint required for training of the walking trainee, and numerically or graphically displaying the information and commands, and controlling driving states of the walking-assist robot (100), the treadmill (200) and the load hoist (300), the operating method comprising:
an information input step of acquiring the size of the body of the walking trainee, information about a walking pattern obtained through a gait training or a walking test, and information or commands required to drive and set the walking-assist robot (100), the treadmill (200) and the load hoist (300) by transferring them from a server of a network system or an information storage device of the controller (400) or by receiving them through an operation of an input terminal of an input unit (410) of the controller;
a robot driving step of driving the walking-assist robot (100), the treadmill (200) and the load hoist (300) in a specific pattern specified by the information or commands input in the information input step;
a training data generating step of receiving information about speed, angle and torque of each joint of the walking trainee under the gait training in the specific pattern in the robot driving step in real time, and selectively classifying and storing the information inputted in real time in the information storage of the controller; and
a training data output step of outputting the information inputted or stored in the training data generating step on a screen of the monitor (420) of the controller in real time;
wherein, in the training data output step, both the information about the angle, speed, rotational force and hoist level of each joint in a standard type appropriate for the walking trainee previously inputted in the information input step and the information about the angle, speed, rotational force, and hoist level of each joint inputted in real time in the training data generating step are displayed together on one screen.

* * * * *